US010285738B1

(12) United States Patent
Doubler et al.

(10) Patent No.: US 10,285,738 B1
(45) Date of Patent: May 14, 2019

(54) POLYAXIAL BALL AND SOCKET FASTENER WITH SPOT WELDED BLOCKING RING

(71) Applicant: Spinal LLC, Palm Beach Gardens, FL (US)

(72) Inventors: Robert L. Doubler, Monroe, MI (US); John E. Hammill, Sr., Maumee, OH (US)

(73) Assignee: Spinal LLC, Palm Beach Gardens, FL (US)

( * ) Notice: Subject to any disclaimer, the term of this patent is extended or adjusted under 35 U.S.C. 154(b) by 0 days.

(21) Appl. No.: 16/190,378

(22) Filed: Nov. 14, 2018

Related U.S. Application Data

(63) Continuation-in-part of application No. 16/040,809, filed on Jul. 20, 2018, which is a continuation-in-part of application No. 15/839,179, filed on Dec. 12, 2017.

(51) Int. Cl.
*A61B 17/70* (2006.01)

(52) U.S. Cl.
CPC ...... *A61B 17/7037* (2013.01); *A61B 17/7032* (2013.01)

(58) Field of Classification Search
CPC .......... A61B 17/8605–17/866; A61B 17/7001; A61B 17/7032–17/7046
See application file for complete search history.

(56) References Cited

U.S. PATENT DOCUMENTS

| | | | | |
|---|---|---|---|---|
| 2007/0118117 A1* | 5/2007 | Altarac | ............... | A61B 17/7037 606/270 |
| 2008/0015579 A1* | 1/2008 | Whipple | ............ | A61B 17/7037 606/250 |
| 2012/0232598 A1* | 9/2012 | Hestad | ............... | A61B 17/7037 606/305 |
| 2015/0142059 A1* | 5/2015 | Biedermann | ...... | A61B 17/7037 606/266 |
| 2015/0201972 A1* | 7/2015 | Doubler | ............ | A61B 17/7002 606/266 |
| 2015/0282844 A1* | 10/2015 | Vedula | ............... | A61B 17/7032 606/305 |
| 2016/0296256 A1* | 10/2016 | Chandanson | ...... | A61B 17/7037 |
| 2017/0281241 A1* | 10/2017 | Jackson | ............ | A61B 17/7037 |
| 2018/0325569 A1* | 11/2018 | Ramsay | ............. | A61B 17/8605 |

* cited by examiner

*Primary Examiner* — Ellen C Hammond
*Assistant Examiner* — Tessa M Matthews
(74) *Attorney, Agent, or Firm* — McHale & Slavin, P.A.

(57) ABSTRACT

The bottom loading fastening system that consists of the polyaxial ball and socket joint used in conjunction with a bone screw. The system allows attachment to a bone screw using a retaining ring spot welded to a blocker ring to assure proper ring positioning. Upon installation the retainer wall is expanded causing a break from the blocker ring producing an audible and tactile indication that the sufficient force has been applied to set the retainer and blocker rings locking the bone screw to a U-shaped connecting assembly.

9 Claims, 10 Drawing Sheets

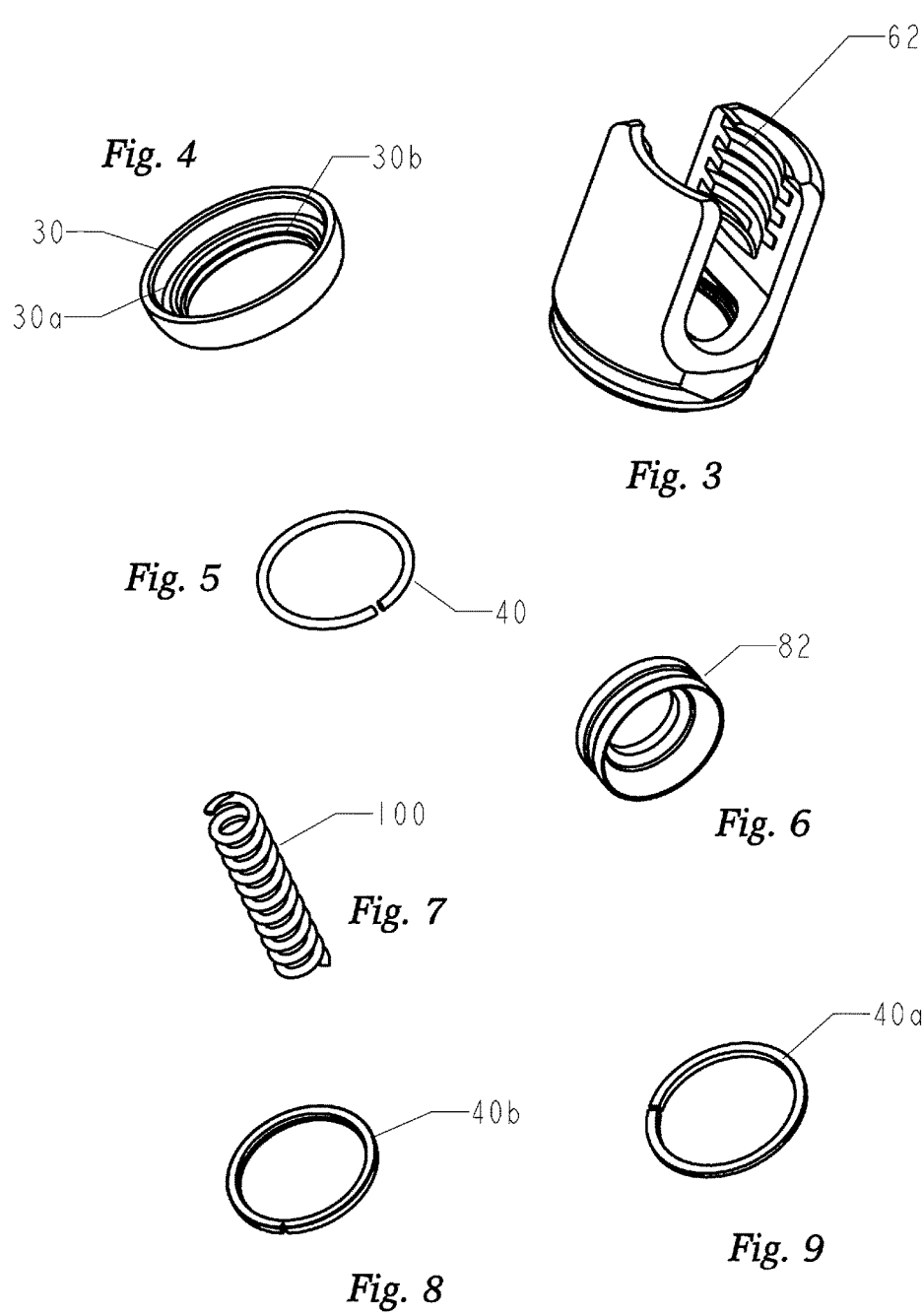

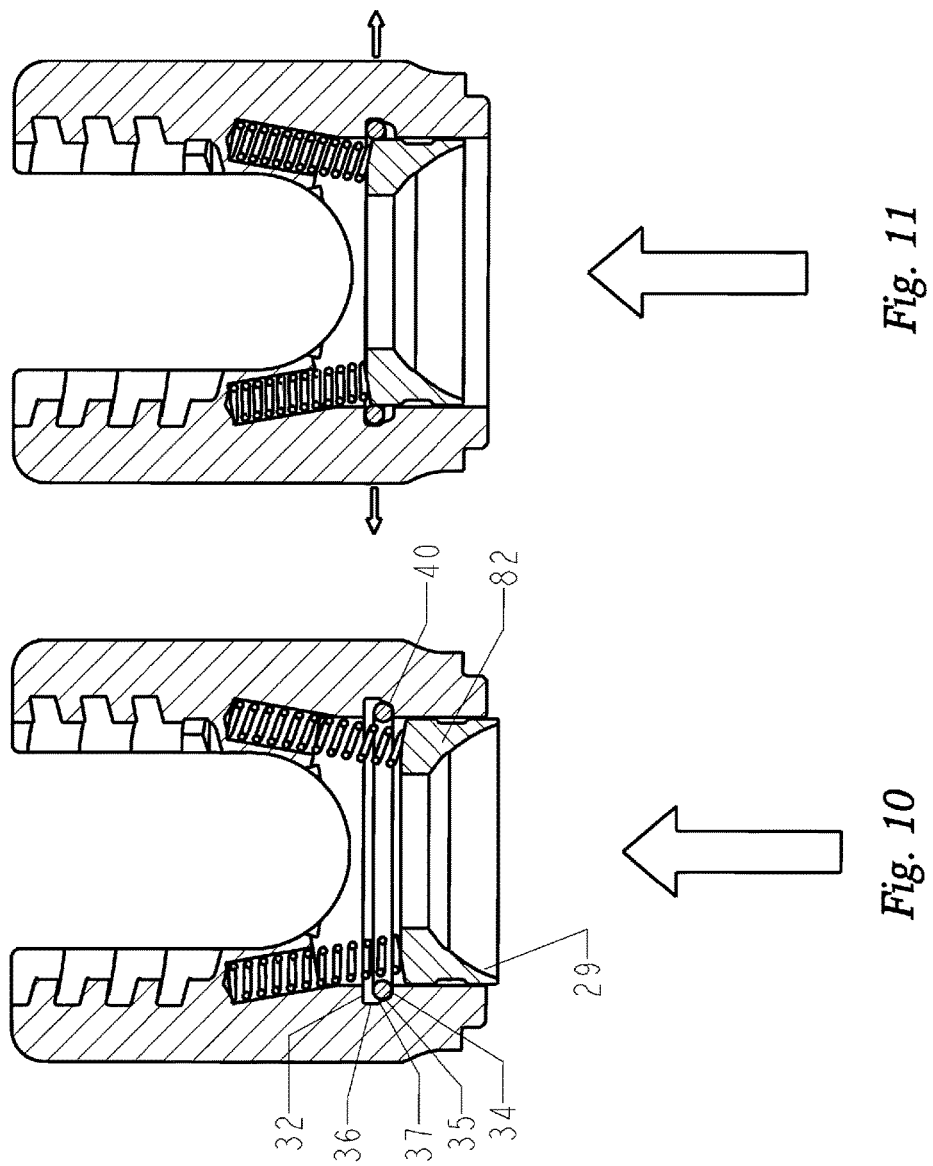

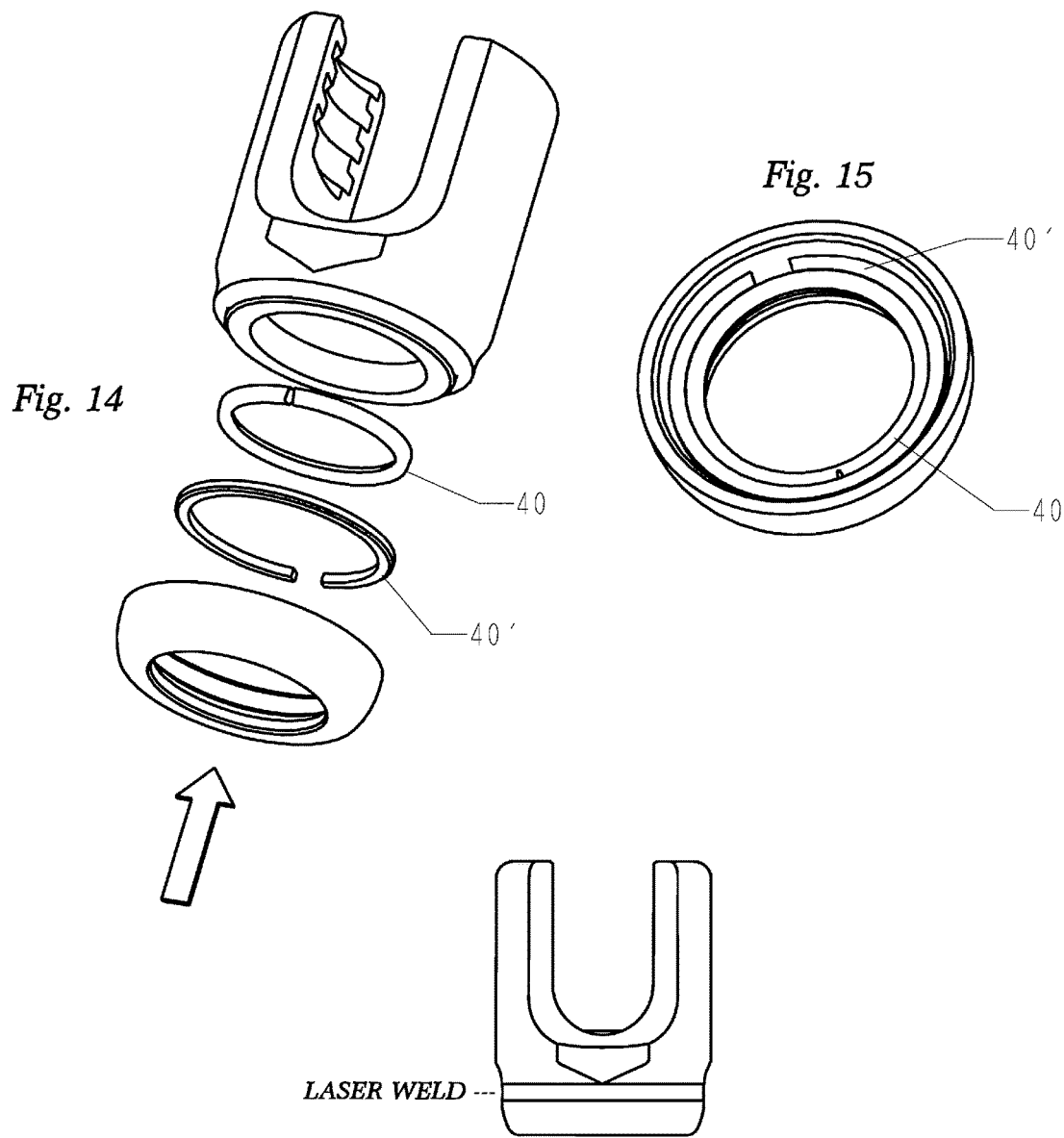

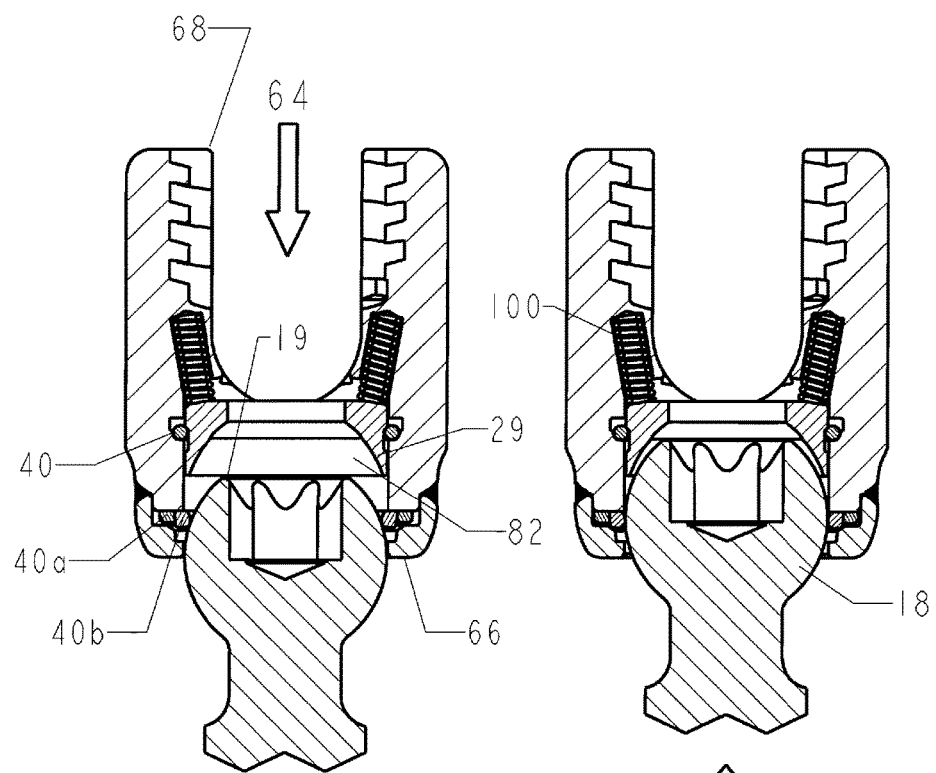
*Fig. 17*  *Fig. 19*
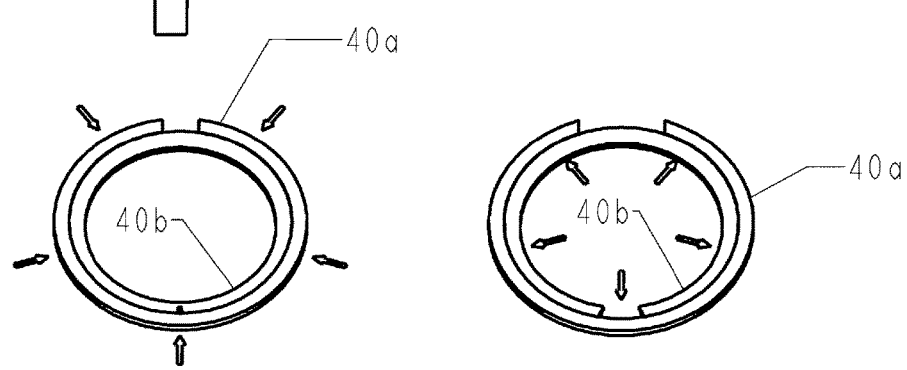
*Fig. 18*  *Fig. 20*

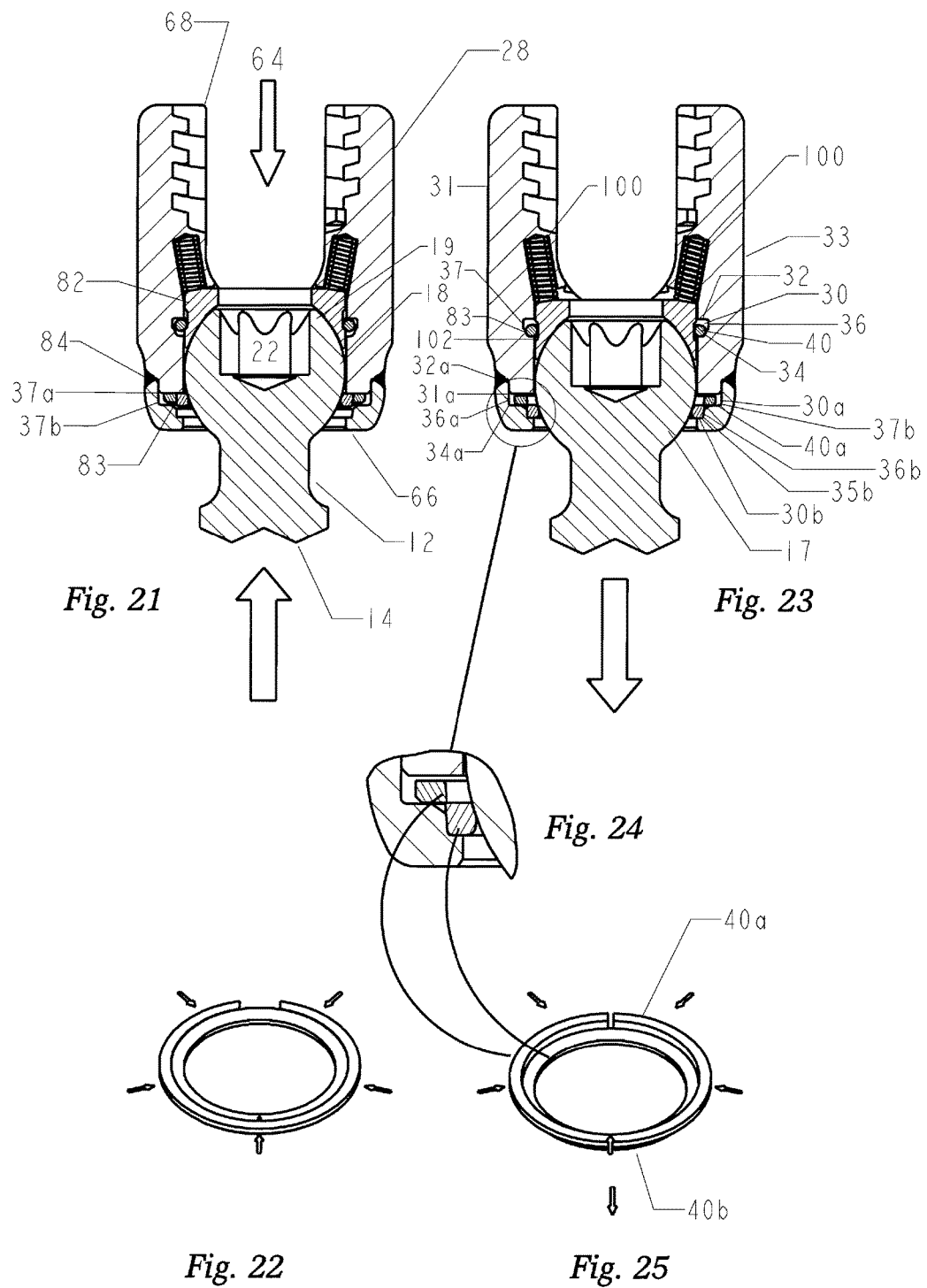

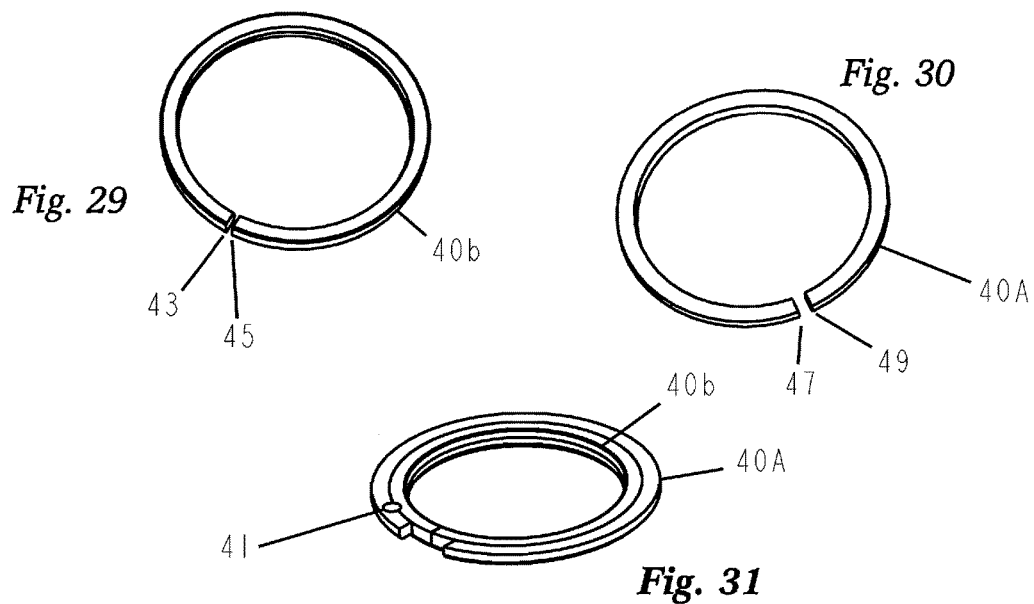
*Fig. 29* *Fig. 30*
*Fig. 31*
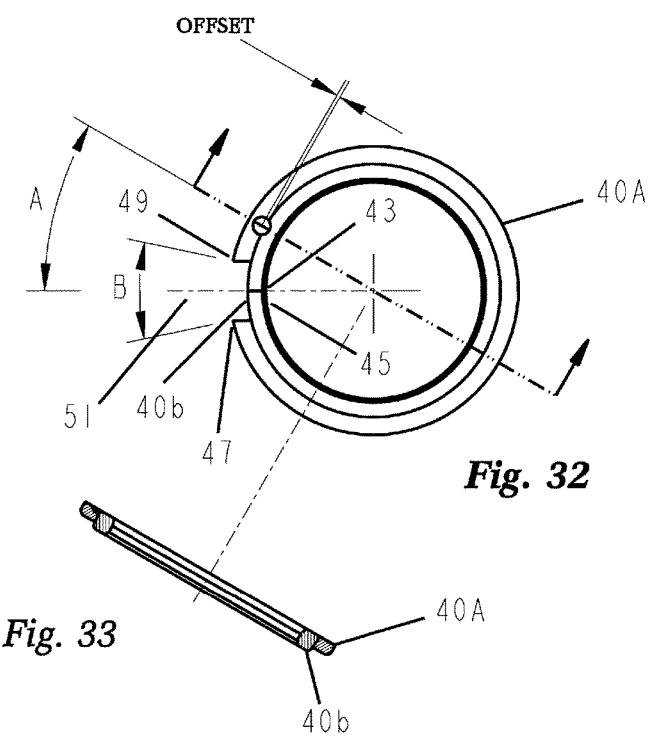
*Fig. 32*
*Fig. 33*

POLYAXIAL BALL AND SOCKET FASTENER WITH SPOT WELDED BLOCKING RING

PRIORITY CLAIM

In accordance with 37 C.F.R. 1.76, a claim of priority is included in an Application Data Sheet filed concurrently herewith. Accordingly, the present invention claims priority as a continuation-in-part of U.S. patent application Ser. No. 16/040,809, entitled "BOTTOM LOADING POLYAXIAL BALL AND SOCKET FASTENER WITH BLOCKING RING WITH NOTCHED SPLIT RING", filed Jul. 20, 2018, which is a continuation-in-part of U.S. patent application Ser. No. 15/839,179, entitled "SPRING CLIP BOTTOM LOADING POLYAXIAL BALL AND SOCKET FASTENER", filed Dec. 12, 2017, incorporated herein by reference.

FIELD OF THE INVENTION

This invention is directed to the field of ball and socket fasteners, and in particular to a polyaxial ball and socket fastener incorporating a blocking ring that is spot welded to a retainer ring adapted for use in a bottom mounted polyaxial ball.

BACKGROUND OF THE INVENTION

In the field of spinal pathologies, the development of spinal fixation devices represents a major medical breakthrough. Surgically implanted fixation systems are commonly used to correct a variety of back structure problems, including those which occur as a result of trauma or improper development during growth. A commonly applied fixation system includes the use of one or more stabilizing rods aligned in a desired orientation with respect to a patient's spine. Anchoring screws are inserted into the patient's spinal bones, and a series of connectors are used to rigidly link the rods and anchors.

A variety of designs exist, with each design addressing various aspects of the difficulties that arise when one reshapes an individual's spine to follow a preferred curvature. Known spinal implant systems often correct one set of problems only to create new ones.

Common to all spinal implant systems is the necessity for proper anchoring to the bone so as to provide support for the aforementioned components. While bone screws are commonly used for anchoring, the use of a polyaxial design has proven very effective in allowing a surgeon the flexibility to secure an installation with minimal strain on the individual.

For this and other reasons, screws located in bone structure typically use a polyaxial base and a specially designed connector member for attachment to a component such as an alignment rod. A problem with the current technology is that bone structure cannot be determined until the patient's bone is exposed. This problem requires a large inventory of various sized implants to be on hand during every surgery. The surgeon must search through the inventory to assemble a combination based on his prediction of what will be required. Even if an implant combination is predicted, the anchoring screw may still require angular insertion due to muscle structure or nerve locations. Any movement of muscle and other tissue increases the difficulty of the operation and can be a major trauma to the patient. Still yet, bone condition may require oversize threads to achieve a suitable purchase to the bone. As a consequence, the surgeon must either maintain a large inventory of anchoring devices, or have a vendor standing by with a large inventory of anchoring devices that will hopefully meet the individual requirements.

One of the problems with a polyaxial pedicle screw is the lack of a stabilized angular placement position during installation. Once a polyaxial pedicle screw is inserted into the bone, the connector component portion has yet to receive a connecting rod leaving the connector assembly to flop over making it difficult for the Surgeon to grasp while in the midst of surgery. This problem is compounded by the need to align multiple component heads for receipt of a connecting rod.

Disclosures related to polyaxial pedical screws are exemplified by the following patents; U.S. Pat. Nos. 7,066,937; 7,947,065; 8,075,603; 8,465,065; 6,485,491; 5,133,717; 5,129,900; 4,887,595; 4,946,458; 5,002,542; 4,854,304; 4,887,596; 4,836,196; 5,800,435; 5,591,166; 5,569,247; 5,716,357; 5,129,900; 5,549,608; 6,716,214; 6,565,567; 5,501,684; 4,693,240; 4,483,334; 4,273,116; 6,672,788; 4,708,510; 3,433,510; 7,445,627 and U.S. Publication Numbers 2008/0177322; 2006/0241599; 2006/0235392; 2006/0155277; 2006/0149240; 2003/0118395 and 2008/0269809.

SUMMARY OF THE INVENTION

Briefly, the present invention is a bottom loading polyaxial ball and socket joint fixation system capable of a snap together assembly. The fixation system includes the polyaxial ball having a bone screw extending outwardly therefrom for use in anchoring to the spine and a connector member that includes a socket constructed and arranged to accept the polyaxial ball. Upon placement of the bone screw, the connector member can be attached to the bone screw. In the disclosed embodiment, the connector member is illustrated as a U-shaped connector member having at least one groove at the base of the connector. The groove operates as a socket for housing a split ring retainer and a blocker split ring. The U-shaped connector further comprises at least one cavity or borehole which extends upwards from the junction or interface between the U-shaped connector and anchor cap into the body of the U-shaped connector. The boreholes or cavities can be at an angle less than or equal to 90 degrees with respect to the interface between the anchor cap and U-shaped connector. The interface between the anchor cap and U-shaped assembly is in general, a planar surface. Within the socket is an anchor cap for receipt of the spherical ball connector. The anchor cap comprises a planar surface and at least one compressible or non-compressible member which fit into the one or more cavities or boreholes of the U-shaped connector.

The socket is receptive to the spherical connector which is inserted through an aperture in the bottom of the connector assembly where the spherical polyaxial ball contacts a split retainer ring that is spot welded to a blocker ring. With sufficient pressure causing a momentary displacement thereof of the split retainer ring, the spot weld is released from the blocker ring allowing the polyaxial ball to pass through the split retainer ring for positioning in the socket.

Once the ball has past through the split retainer ring the blocker ring prevents the split retainer ring from moving into an area that would otherwise allow opening. The blocker ring essentially removes the space between the outer diameter of the retainer ring and the inner diameter of the spherical connector.

A set screw or nut can then be utilized to press a connecting rod into contact with the ball while simultaneously causing the lower portion of the spherical ball connector to wedge against the inner surface of the connector member immobilizing the connection.

During surgery a surgeon can determine the most advantageous bone screw or other type of bone connection to match the connecting assembly. After inserting the bone screw into the desired location, the bone connector is then coupled to the connector assembly by inserting or snapping the spherical connector into the socket of the connecting assembly. In operation, the spherical connector is pushed past the retainer rings whereby the rings snap past the largest diameter of the connector to prohibit removal of the connector while still allowing polyaxial movement between the spherical ball and the connector member. In the preferred embodiment, the retainer rings are resiliently biased against a lower and an upper surface of the spherical connector and engage the spherical connector so as to keep the U-shaped connector member in position during installation. The compressible or non-compressible members of the anchor cap provide further stability so as to keep the U-shaped connector member in position during installation. A surgeon can easily move the spherical connector member into a preferred position and the resilient split ring will keep sufficient force between the lower surface of the spherical connector and the groove so as to maintain the spherical connector in a selected position relative to the connector assembly. This facilitates the installation of the rod as the U-shaped connector not only can be rotated into a position for proper placement of the connecting rod but the proper angle of the U-shaped connector can also be maintained while allowing the surgeon to align additional screws for ease of rod placement.

Because of the flexibility and resilience of the retaining rings, the mating parts do not require fine tolerances and are economical to manufacture. The system is modular, employing a collection of anchoring assemblies that are linked, via various connectors, to strategically-arranged stabilizing rods.

The connector members are rigid structures adapted to link an associated anchoring assembly with one of the stabilizing rods. The stabilizing rods may be rigid or dynamic members shaped to form a spine-curvature-correcting and/or immobilizing path. Attaching each anchoring assembly, via connectors, to a stabilizing rod forces a patient's back into a surgeon-chosen shape. Stabilizing rods may be used singly, or in pairs, depending upon the type of correction required. The rods vary in size, but typically extend between at least two vertebrae.

Accordingly, it is an objective of the present invention to teach the use of a bottom loading polyaxial ball and socket fastener for use in a spinal stabilization system utilizing a split retainer ring that is spot welded to a blocker ring that allows insertion of a pedicle polyaxial ball and the split ring is then stopped from reopening by the blocker ring.

Another objective of the invention is to disclose the use of a polyaxial ball and socket system that is capable of securing various anchors to various connector members so as to reduce the amount of inventory required to meet a particular installation.

It is another objective of the present invention to provide a polyaxial bone screw assembly for a spinal fixation system that permits component adjustment during installation, thereby enabling satisfactory correction of a wide variety of spinal deformities.

It is an additional objective of the present invention to provide a bone screw assembly that includes a split ring locking mechanism that is simple, strong and reliable. Wherein a blocker ring is spot welded to a retainer ring and, once the retainer ring is detached from the blocker ring, the retainer ring is held in place by an interference fit between the outer diameter of the retainer ring and inner diameter of the blocker ring.

Another objective of the invention is to teach the use of a retainer ring formed from a 360 degree ring that is released from a blocker ring when the spherical head of a screw is forced through the retainer ring during assembly. The spot weld providing a tactile feel when the weld is split from the retainer ring.

Another objective of the invention to provide a spinal fixation system that has an audible sound as well as a tactile feel when the spherical ball causes the spot weld to release the split ring from the blocker ring.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

FIG. 3 is a perspective view of the U-shaped connector;

FIG. 4 is a perspective view of the annulus formed at the distal end of the U-shaped connector and grooves therein for receipt of a retaining ring;

FIG. 5 is a perspective view of a split-ring;

FIG. 6 is a perspective view of an anchor cap;

FIG. 7 is a perspective view of a compressible member;

FIG. 8 is a perspective view of a split ring constructed and arranged to fit into a retention ring;

FIG. 9 is a perspective view of a retention ring constructed and arranged to receive a split ring of FIG. 8;

FIGS. 10 to 13 are cross-sectional views of the U-shaped connector illustrating the insertion of the anchor cap;

FIG. 14 is a perspective view of the various sections of the U-shaped connector;

FIG. 15 is a perspective view of a split ring and a retention ring disposed in a ring groove of the annulus formed at the distal end of the U-shaped connector;

FIG. 16 is a plane view of the U-shaped connector;

FIG. 17 is a cross-sectional view of the ball and socket fastener with the anchoring member illustrating the initial step of the insertion of a bone screw into the U-shaped connector member;

FIG. 18 is a perspective view of the positioning of the split ring and retaining ring of the assembly in FIG. 17;

FIG. 19 is a cross sectional view of the ball and socket fastener with the anchoring member illustrating a step in the capturing of the head of the bone screw;

FIG. 20 is a perspective view of the positioning of the split ring and retaining ring of the assembly in FIG. 19;

FIG. 21 is a perspective view of the ball and socket fastener with the anchoring member illustrating the cooperation between the spherical ball and the connector member;

FIG. 22 is a perspective view of retaining rings illustrating the interaction between the two retaining rings when the assembly is in the locked position illustrated in FIG. 21;

FIG. 23 is a perspective view of the ball and socket fastener with the anchoring member illustrating the polyaxial cooperation between the spherical ball and the U-shaped connector member in an unlocked position;

FIG. 24 is a perspective view of the grooves which accommodate the retaining rings shown in FIG. 22;

FIG. 25 is a perspective view of the retaining rings shown in FIG. 22 illustrating the interaction between the two retaining rings when the assembly is in an unlocked position, illustrated in FIG. 23;

FIG. 29 is a perspective view of the retainer ring;

FIG. 30 is a perspective view of the blocker ring;

FIG. 31 is a perspective view of the retainer ring spot welded to the blocker ring;

FIG. 32 is a top plane view of FIG. 31; and

FIG. 33 is a cross sectional side view of FIG. 32.

DETAILED DESCRIPTION OF THE PREFERRED EMBODIMENT

Figure 1:
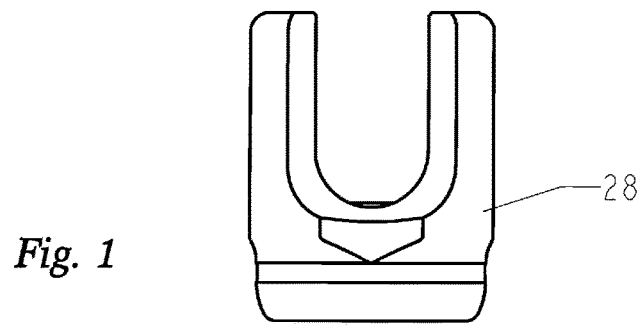
FIG. 1 is aside view of the U-shaped connector.

While the present invention is susceptible of embodiments in various forms, there is shown in the drawings and will hereinafter be described a presently preferred embodiment with the understanding that the present disclosure is to be considered an exemplification of the invention and is not intended to limit the invention to the specific embodiments illustrated.

The terminology used herein is for the purpose of describing particular embodiments only and is not intended to be limiting of the invention.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used in this specification and the appended claims, the term "or" is generally employed in its sense including "and/or" unless the content clearly dictates otherwise.

For purposes of this disclosure, "proximal" refers to the end closer to the device operator during use, and "distal" refers to the end farther from the device operator during use.

Referring generally to the Figures, disclosed is an exemplary embodiment of the polyaxial ball and socket fastening system adapted for use in a spinal fixation system. The fastening system includes a spherical ball connector (18) secured or formed integrally with a bone anchor (12) and connecting assembly that includes a snap-in type receptacle for the spherical ball connector (18) to form a polyaxial joint allowing a range of motion (ROM). The connector assembly (28) also includes a receiver that may be used in conjunction with a connecting rod member (70) for securing at least two bone anchors (12) together.

The bone anchor (12) of the preferred embodiment is a bone anchor (12) including a shank (14) having a length with at least one helical thread (16) formed along the length thereof. It is important to note that the proportions of the bone anchor (12) depicted are for illustrative purposes only and variations in the length of the shank, diameter of the screw, thread pitch, thread length, number of thread leads, shank induced compression and the like may be varied without departing from the scope of the invention. At the upper or proximal end (20) of the shank (14) is a ball shaped spherical ball connector (18) having a predetermined diameter. A driver receptacle (22), which may be configured as a plurality of recesses or a single recess for an insertable driver tool, is located along the upper portion (19) of the spherical ball connector (18) for use in installing the bone anchor (12) by use of a driving tool. It should be noted that the driver receptacle (22) may be any shape, male or female, suitable for cooperation with a driving tool to rotate the bone anchor (12) into its final position.

As particularly illustrated in FIGS. 21-25 and 29-33, a U-shaped connector assembly (28) includes a first retaining ring (40), a blocking ring (40a) and a second retaining ring (40b) that is insertable into a first (30), a second (30a) and second retaining ring groove (30b) respectively. The first retaining ring (40) and a second retaining ring (40b) are split retaining rings, the blocking ring (40a) is a split ring shaped and sized to snap over the circumference of the second split retaining ring (40b) when the spherical ball connector is pushed upwards. The blocking ring (40a) is welded to the second split retaining ring (40b) by use of a spot weld (41) which maintains the second split ring 40b in place by pinching (interference fit) an outer diameter of the second split retaining ring (40b) with an inner diameter of the blocking ring (40a). The spot weld (41) prevents the second split retaining ring (40b) from separating from the blocker ring during post modular head assembly steps and product handling. The blocking ring (40a) increases the width of the cross section as compared with the ring "40a" set forth in U.S. Pat. No. 9,615,858. When assembling the modular head with a pedicle screw, the push down force fractures the spot weld allowing the second split retaining ring (40b) to be forced down as the blocker ring contracts to a memory position, over top, blocking any upward motion of the second split retaining ring (40b). The push down capture force is controlled by the spot weld, diameter, penetration (depth) and offset location. In the preferred embodiment the spot weld (41) is offset a predetermined amount as depicted in FIG. 32.

The blocker ring (40a), when welded to the second split retaining ring (40b) maintains the split between ends (43) and (45) in a substantially closed position. The second split retaining ring (40b) is press fit into the blocker ring (40a). The ends (47, 49) of the blocker ring (40a) are flared closing the split on the second split retaining ring (40b). The ends (47, 49) are equally spaced apart from the blocker ends (43, 45). The spot weld (41) is made at about a 1 o'clock position when the space (51) between ends (47, 49) is considered the 12 o'clock position. The retaining and blocking rings (40a, 40b) are made of a biocompatible spring temper material which may include shape memory alloys and in a preferred embodiment is stainless steel.

The spot weld (41) is a single pulse laser spot weld (tack weld). The spot weld (41) is constructed and arranged to split when a predetermined force is applied to the second split retaining ring 40b resulting in a tactile feel and an audible sound. The tactile feel can be felt at the moment of the spot weld break, and the snap of the ring material provides a sound that can be clearly heard during the installation step. The tactile feel and audible sound provide a surgeon with positive reinforcement that that the split retainer ring has been pressed against the spherical head of the screw with sufficient force to cause the spherical head to pass the second split retainer ring (40b).

Figures 12, 13:
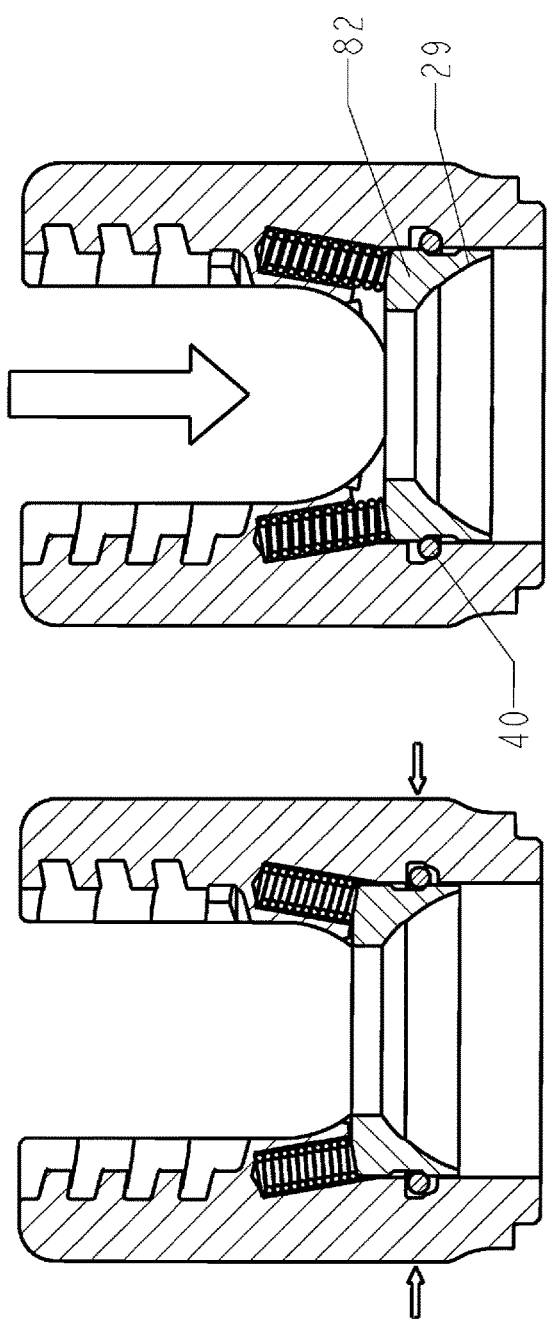
Figure 26:
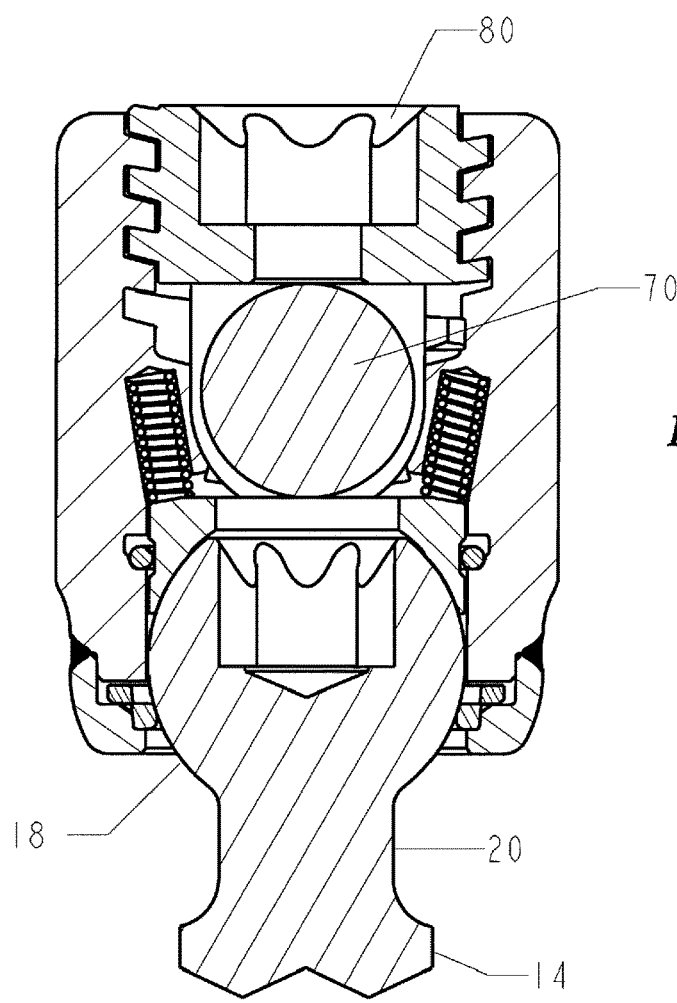
FIG. 26 is a perspective view of a set screw.
Figure 27:
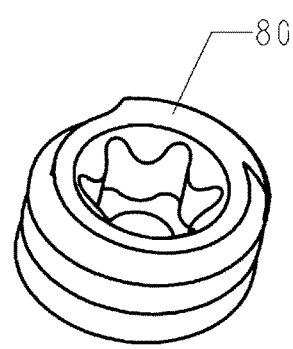
FIG. 27 is a plane view of the assembled ball and socket fastener.

In some embodiments, the U-shaped connector assembly comprises at first retaining ring (40), preferably a split retaining ring. This is illustrated in FIGS. 10 through 13. As the anchor cap (82) of the U-shaped connector assembly is pushed upwards during the capture of the spherical ball connector (18) (not shown), the first retaining ring (40) expands and slides up the side wall (36) to a displaced position at the second annulus (37). Once past the greatest diameter of the spherical ball connector (18) the first retaining ring (40) will contract and slide back down the side wall (36) from its displaced position at the second annulus (37) to its normal position along the lower end wall (34) as illustrated in FIG. 12. The spacing of the first split retaining ring (40) within the split ring groove (30) and the material of the first split retaining ring (40) provides a biasing force that ensures that the first split retaining ring (40) will not bend as the spherical ball connector (18) passes the first split retaining ring (40). After the spherical ball connector (18) has been captured by the first split retaining ring (40), the first split retaining ring (40) will thereafter serve to maintain a slight upward force on the spherical ball connector (18) as the first split retaining ring (40) attempts to contract to a diameter smaller than the diameter (D1) of the first annulus (35). The upward biasing force created by the first split retaining ring (40) creates a frictional engagement of the spherical ball connector (18) with the lower end wall (34) and the side wall (36) and the lower portion (17) of the spherical ball connector (18) as illustrated in FIG. 13.

Figure 2:
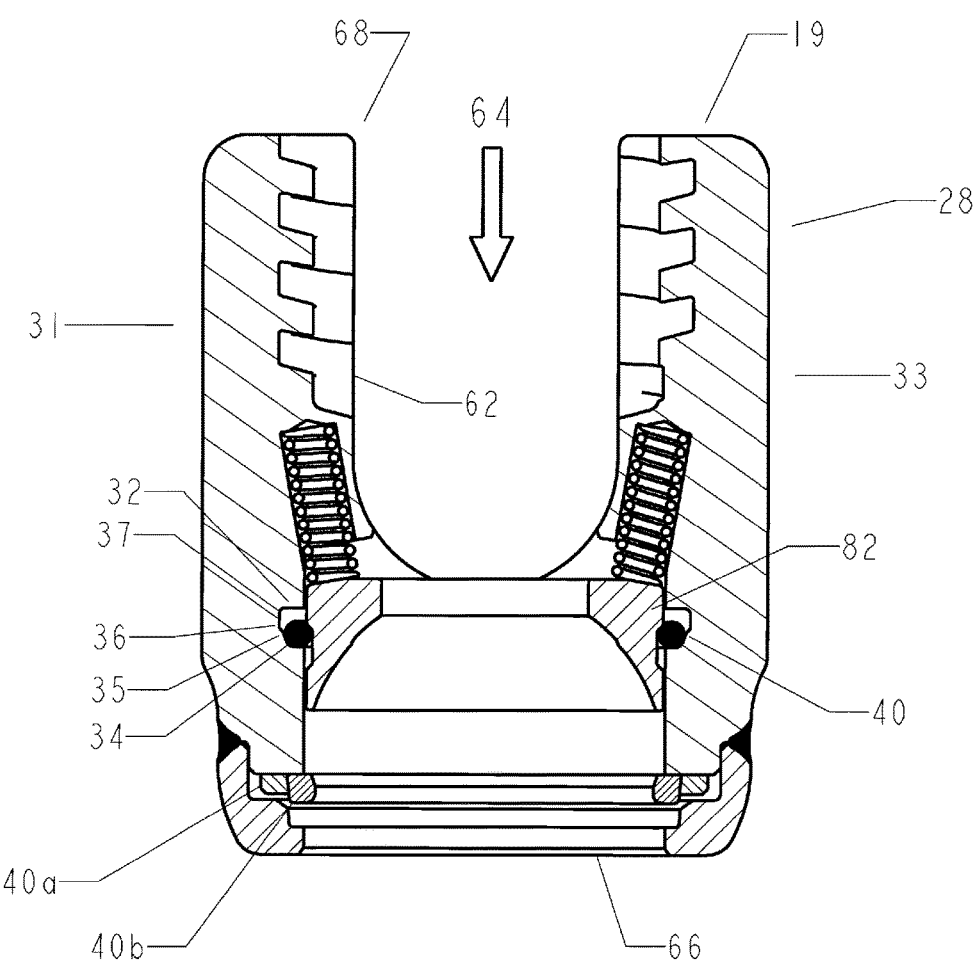
FIG. 2 is a cross sectional view of the U-shaped connector and anchor cap.

As illustrated in FIGS. 2, 21 and 23, the U-shaped connector assembly (28) includes an internal passageway (64) that extends from a first or distal end (66) to a second or proximal end (68). The diameter of the internal passageway (64) being greater than the diameter of the spherical ball connector (18) at said first end (66) and the diameter of the internal passageway (64) at said second end (68) being smaller than the diameter of the spherical ball connector (18). The U-shaped connector assembly (28) includes a base with a pair of U-shaped openings forming a first upstanding side wall (31) and second side wall (33).

Shown in FIG. 21, the first retaining ring groove (30) is further defined by upper end wall (32), a lower end wall (34) and a side wall (36) therebetween. The side wall (36) is angularly positioned wherein the junction of the lower end wall (34) and side wall (36) forms a first annulus (35) having a first diameter (D1) and the junction of the upper end wall (32) and side wall (36) forms a second annulus (37) with a second diameter (D2), larger than the first diameter (D1).

Shown in FIGS. 21 and 23, the blocking ring groove (30a) is further defined by upper end wall (32a), a lower end wall (34a) and a side wall (36a) therebetween. The side wall (36a) can be vertically or angularly positioned wherein the junction of the lower end wall (34a) and side wall (36a) forms a first annulus (35a) having a first diameter (D1a) and the junction of the upper end wall (32a) and side wall (36a) forms a second annulus (37a) with a second diameter (D2a). The second diameter (D2a) is larger than the first diameter (D1a) when the side wall (36a) is angularly positioned.

Shown in FIGS. 21 and 23, the second retaining ring groove (30b) is further defined by upper end wall (32b), a lower end wall (34b) and a side wall (36b) therebetween. The side wall (36b) can be vertically or angularly positioned wherein the junction of the lower end wall (34b) and side wall (36b) forms a first annulus (35b) having a first diameter (D1b) and the junction of the upper end wall (32b) and side wall (36b) forms a second annulus (37b) with a second diameter (D2b). The second diameter (D2a) is larger than the first diameter (D1a) when the side wall (36b) is angularly positioned.

In embodiments, the diameter (D1a) of the first annulus (35a) and the diameter (D2a) of the second annulus (37a) of the second groove (30a) is greater than (i) the diameter (D1b) of the first annulus (35b) and (ii) the diameter (D2b) of the second annulus (37b) of the second groove (30b). In such an embodiment, the blocking ring (40a) is larger in diameter than the second retaining ring (40b) wherein the second split retaining ring (40b) is positioned around the blocking ring (40a) when the spherical ball connector is pushed upwards so that the second groove (30a) now contains the blocking ring (40a) and second split retaining ring (40b) which have expanded to tightly fit into the second groove (30a).

In assembly, the shank (14) of the bone anchor (12) is inserted into the pedicle of a patient by use of a driving tool (not shown), fixing the position of the bone anchor (12). The U-shaped connector assembly (28) can then be attached over the spherical ball connector (18) of the bone anchor (12), wherein the spherical ball connector (18) engages the retaining and blocking rings (40, 40a, 40b). FIG. 23 is a cross sectional view of the spherical ball connector (18) in the process of assembly to the socket of the U-shaped connector assembly (28) by placement against the retaining and blocking rings (40, 40a, 40b). Referring now to FIG. 21, as the U-shaped connector (28) contacts the spherical ball connector (18), the blocker ring and second split ring (40a, 40b), positioned in split ring grooves (30a, 30b), contact the spherical ball connector (18) and are moved from their normal positions along the lower end walls (34a, 34b) to a position along the upper end walls (32a, 32b) respectively. At the widest point of the spherical ball connector (18) contacts the second split retaining ring (40b), the second split retaining ring (40b) expands in diameter along the upper end wall (32b) approaching the second annulus (37b). In this position the second split retaining ring (40b) is able to expand up to the diameter of the blocking ring (40a) which expands into the diameter (D2a) presented by the second annulus (37a) allowing the second split retaining ring (40b) to pass the spherical ball connector (18) which allows the U-shaped connector (28) to engage the spherical ball connector (18). The blocking ring (40a) exerts an inward force against the second split retaining ring (40b) so that the spherical ball connector is held in position as the upward biasing force created by the blocking ring and second retaining rings (40a, 40b) creates a frictional engagement of the spherical ball connector (18) with the lower end wall (34a) and the side wall (36a) and the lower portion (17a) of the spherical ball connector (18).

In some embodiments the first retaining ring (40), is a split retaining ring. In assembly, once this first retaining ring (40) is past the spherical ball connector (18), the first split retaining ring (40) will contract and slide back down the side wall (36) from its displaced position at the second annulus (37) to its normal position along the lower end wall (34), returning to diameter (D1). In this position the first split retaining ring (40) prohibits the spherical ball connector (18) from removal, as shown in FIG. 21. The more pressure that is applied in a removal attempt, the more resistance is provided by the first split retaining ring (40) as it is frictionally engaged between the spherical ball connector (18), the lower end wall (34), and the sidewall (36).

The spacing of the first split retaining ring (40) within the split ring groove (30) and the material of the first split retaining ring (40) provides a biasing force that ensures that the first split retaining ring (40) will not bend as the spherical ball connector (18) passes the first split retaining ring (40). After the spherical ball connector (18) has been captured by the first split retaining ring (40), the first split retaining ring (40) will thereafter serve to maintain a slight upward force on the spherical ball connector (18) as the first split retaining ring (40) attempts to contract to a diameter smaller than the diameter (D1) of the first annulus (35). The upward biasing force created by the first split retaining ring (40) creates a frictional engagement of the spherical ball connector (18) with the lower end wall (34) and the side wall (36) and the lower portion (17) of the spherical ball connector (18). The split retaining ring provides a tactile feel wherein the retainer clip snaps into position to indicate proper installation.

The anchor cap (82) comprises a first retaining ring (40), which is used to provide additional stability to the connector assembly during and after insertion into the bone of a patient. The anchor cap (82) has a spherical surface formed on a lower end (84) which provides a seat for the spherical ball connector (18), and can be inserted into the internal passageway of the U-shaped connector assembly (28) to engage with the first retaining ring (40) in a first split ring groove (30). The anchor cap (82) seats with and is resiliently biased against an upper portion (19) of the spherical ball connector (18) and engages the spherical ball connector (18) so as to keep the U-shaped connector assembly (28) in position during installation. The anchor cap (82) comprises at least one compressible or non-compressible member (100) which extends from the top of the anchor cap in an upward direction distal to the anchor cap (82) and into a cavity (101) in the U-shaped connector assembly (28). An example of a compressible member is a spring. An example of a non-compressible member is a screw. Of course, whether a member is compressible or non-compressible will also depend on the composition of the member, e.g., metal, rubber etc. FIGS. 21 and 23 are cross-sectional views of an anchor cap (82). As illustrated in FIGS. 21 and 23, the anchor cap (82) is predominantly cylindrical having an outer surface including an anchor cap groove (30) for engagement with a first retaining ring (40) located in a first ring groove (30) on the inner side surface (29) of the U-shaped connector and the outer surface (102) of the anchor cap (82). The anchor cap (82) has a lower end (84) which is predominantly spherical to engage with and provide a seat for the spherical ball connector (18). As illustrated in FIGS. 21 and 23, as the anchor cap (82), which, is inserted through the bottom of the connector assembly (28) prior to connecting the connector assembly (28) to a bone anchor (12), the first retaining ring (40) moves from its initial position along an upper wall of the first ring groove (30) moving up and expanding outward along a side wall of the first retaining ring groove (32) to a lower wall of the first retaining ring groove (34) and then a lower annulus of the first retaining ring groove (34) to allow the anchor cap (82) to pass. When the anchor cap groove (83) and the first retaining ring groove (30) are in alignment, the first retaining ring (40) will expand, thereby, mechanically connecting the anchor cap (82) to the connector assembly (28). The expansion of the first retaining ring (40) provides a biasing upward force on the anchor cap (82) because of the angled slope of the anchor cap groove (83). In preferred embodiments, the first retaining ring is a split retaining ring.

A bone anchor (14) can be inserted into the connector assembly (28) from the bottom. As the bone anchor (14) is inserted, the first split retaining ring (40) moves in the split ring groove (30) as described above to allow the connector assembly (28) to engage the spherical ball connector (18). As the spherical ball connector (18) passes the first split retaining ring (40), the upper portion (19) of the spherical ball connector (18) comes into contact and seats with the lower end (84) of the anchor cap (82). The first split retaining ring (40) prevents the anchor cap (82) from disengaging with the connector assembly (28).

Illustrated in FIGS. 21 and 23, the seating of the spherical ball connector (18) with the anchor cap (82) creates a frictional engagement between the upper portion (19) of the spherical ball connector (18) and the lower end (83) of the anchor cap (82) caused by the downward force of the anchor cap (82) on the spherical ball connector (18) from the contraction of the retaining and blocking rings (40, 40a, 40b). This frictional engagement between the two surfaces allows the connector assembly (28) to be positioned and maintained at different angles for installation of a connecting rod member (70).

After the anchor cap (82) and spherical ball connector (18) have been inserted into the connector assembly (28), a connecting rod member (70) and set screw (80) can be inserted to lock the connector assembly (28) together. The set screw (80) exerts a force on the connecting rod member (70) which in turn exerts a force on the anchor cap (82), increasing the frictional connection between the anchor cap (82) and the spherical ball connector (18). In this configuration, the spherical ball connector (18) is held more stable by the greater contact surface than without the anchor cap (82) and only the point contact of the connecting rod member (70) on the upper portion (19) of the spherical ball connector (18).

Figure 28:
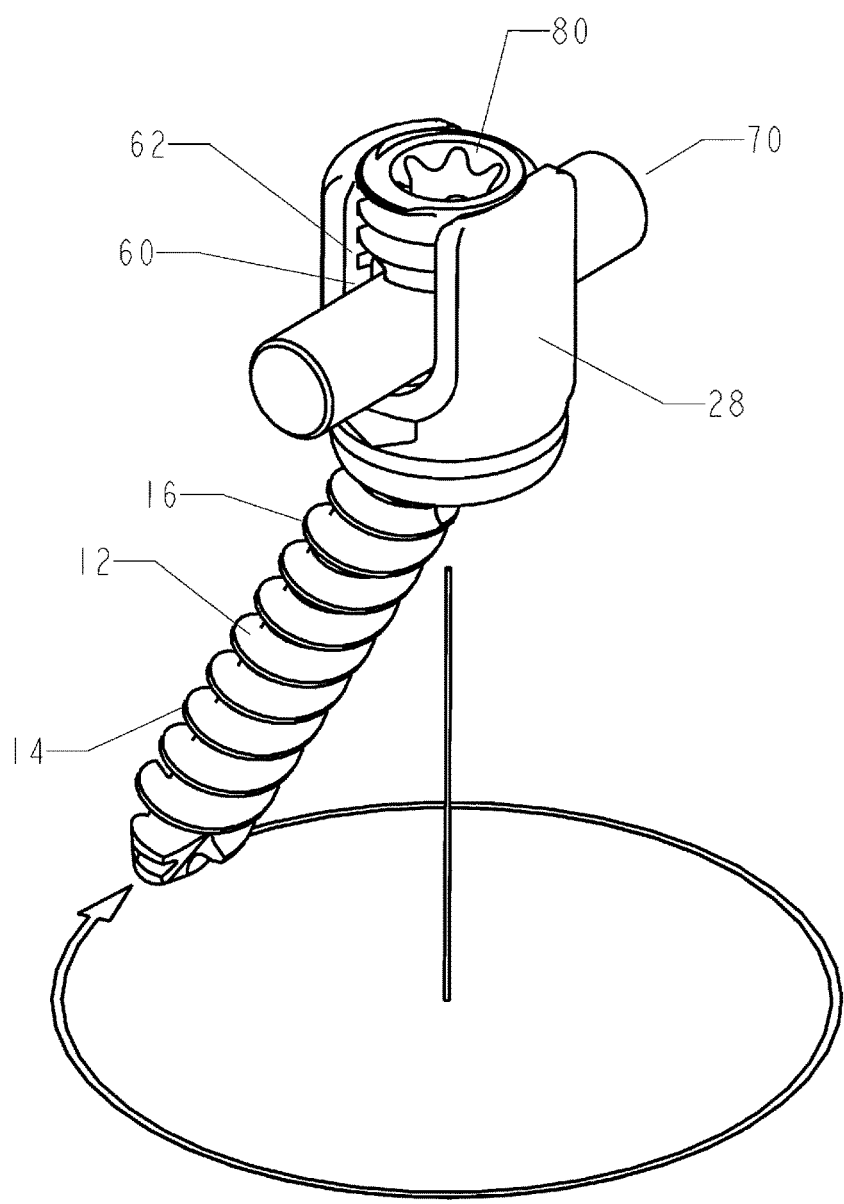
FIG. 28 is a perspective view of the ball and socket fastener with the anchoring member illustrating the polyaxial cooperation between the spherical ball and the connector member.

As illustrated in FIG. 28, once mounted the polyaxial action of the U-shaped connector assembly (28) allows for ease of positioning a connecting rod member (70) into the U-shaped receptacle opening (60). A securing element in the form of a set screw (80) is inserted into the threaded portion (62) of the U-shaped connector assembly (28) until the set screw (80) contacts the connecting rod member (70), causing the connecting rod member (70) to press against the spherical ball connector (18). The insertion of the securing element causes the spherical ball connector (18) to wedge the lower portion (17) of the spherical ball connector (18) against the first split retaining ring (40) thereby securing the assembly in a desired position. The inner side surface (29) of the anchor cap (82) is generally spherical and constructed and arranged in configuration to be complimentary to the spherical surface on the spherical ball connector (18). It should be appreciated that this construction provides a three point contact between the U-shaped connector assembly (28) and the spherical ball connector (18) by capturing the connector rod member (70) therebetween with the set screw (80) allowing for securement.

The set screw (80) can have various socket forms for a driver receptacle, for example, a hex socket, a hexalobular (star shaped) socket, and the like. The socket shape of the set screw (80) is not limited to these two known patterns and can include others such as a square/Robertson type socket, pentagon socket, slotted socket, any of the cruciform socket types, TTAP socket type, or any other socket type which would allow the screw to be securely tightened.

Unique to this invention is the ability for the surgeon to attach various types of bone anchors or the like to the connecting assembly, after having installed the bone anchor into the bone of a patient. While there are a myriad of anchoring devices that can be adapted to include the spherical ball, bone hooks etc., for ease of illustration the bone screw is depicted and it is well known that various lengths and diameters of bone screws are available, many of which would not fit through the inner diameter of the connector assembly. Thread styles, lengths and so forth that are best suited for installation may be estimated before surgery but it is well known that only during actual surgery can the proper style be confirmed. Because it is most difficult to predict the proper combination of anchor screw and connector member, surgeons must either have a large selection of spinal implants to choose from or be forced to use the closest combination and hope that it will suffice.

In embodiments, multiple bone anchor (12) sizes can be accommodated by a single connector assembly (28).

It should be noted that while various types of bone screws have been mentioned, the instant installation allows placement of an anchoring device having a spherical connector into position before a connector member is attached. This provides the surgeon with an option of positioning the bone screw before placement of the connecting member thereby providing a simplified installation should positioning of the anchoring screw be difficult due to muscle or other interference. Installation of a bone screw with the connecting member allows a range of mobility as well as better visual positioning. Further, while the U-shaped connector member is depicted, various types of connector members may be used in combination with the spherical ball connector (18) allowing a surgeon to select the appropriate combination during surgery thereby enhancing the success for the benefit of the patient as well as lowering cost of inventory necessary when estimating the various types of situations that the surgeon may encounter during the operation.

All patents and publications mentioned in this specification are indicative of the levels of those skilled in the art to which the invention pertains. It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A bottom loading connector assembly for polyaxial coupling to an anchored bone screw having a spherical ball with a shank having at least one thread formed along a length of the shank, comprising:
    a connector assembly having a first side wall and a second side wall forming a U-shaped opening, an upper end and a bottom end with a passageway therebetween having a diameter along the bottom end being greater than a diameter of a bone screw spherical ball and a diameter along the upper end being smaller than the diameter of the spherical ball;
    a first groove formed along the lower end of said passageway;
    a retaining ring positionable in said first groove;
    a second groove juxtapositioned to said first groove;
    a blocker split ring spot welded to said retaining ring positionable in said second groove;
    an anchor cap dimensioned to fit over a portion of the spherical ball;
    and a set screw releasably securable to the upper end of said connector assembly;
    wherein said bottom end of said connector assembly is positioned over the spherical ball of an anchored bone screw, said retaining ring and said blocker split ring expands to permit passage of the spherical ball whereby said blocker split ring captures said retaining ring maintaining said retaining ring in position beneath the spherical ball thereby reducing the diameter of the bottom end and preventing removal of said connector assembly from said anchored bone screw.

2. The bottom loading connector assembly for a polyaxial screw as set forth in claim 1, wherein said blocker split ring is shaped and sized to snap over said retaining ring providing about 360 degree coverage.

3. The bottom loading connector assembly for a polyaxial screw set forth in claim 1, wherein said retaining ring has first and second ends centrally positioned between said blocker split ring having first and second ends, said retaining ring is spot welded to said blocker split ring at a position about 1 o'clock from said first and second ends of said retaining ring.

4. The bottom loading connector assembly for a polyaxial screw set forth in claim 1, wherein said retaining ring expands when said spherical ball is installed causing said spot weld to release said blocker split ring, wherein said blocker split ring is moved to a position to prevent said retaining ring from expanding.

5. The bottom loading connector assembly for a polyaxial screw set forth in claim 1 wherein said retaining ring is constructed and arranged to indicate a change in diameter by tactile feel and sound when the retainer ring is positioned over spherical ball and released from said blocker split ring.

6. The bottom loading connector assembly for a polyaxial screw as set forth in claim 1, wherein a side wall of the second groove is angularly positioned and a junction of a lower end wall and said side wall of the second groove forms a first annulus having a first diameter and a junction of a lower end wall and said side wall of the connector assembly forms a second annulus having a second diameter.

7. The bottom loading connector assembly for a polyaxial screw as set forth in claim 6, wherein said second diameter of said second annulus is greater than said first diameter of the first annulus.

8. The bottom loading connector assembly for a polyaxial screw as set forth in claim 1 wherein said retaining ring can expand in diameter within said first groove up to the second diameter of the second annulus as said spherical connector is moved past said retaining ring.

9. The bottom loading connector assembly for a polyaxial screw as set forth in claim 1, wherein said passageway at said first end of said connector assembly has a generally spherical surface and is constructed and arranged in configuration to be complimentary to a spherical surface of said spherical ball.

* * * * *